(12) United States Patent
Nagy

(10) Patent No.: US 10,610,501 B2
(45) Date of Patent: Apr. 7, 2020

(54) METHODS AND MATERIALS FOR REDUCING ISCHEMIA-REPERFUSION INJURY

(71) Applicant: The University of Pécs (Pécsi Tudományegyetem), Pecs (HU)

(72) Inventor: Agnes Nagy, Pecs (HU)

(73) Assignee: The University of Pécs (Pécsi Tudományegyetem), Pecs (HU)

( * ) Notice: Subject to any disclaimer, the term of this patent is extended or adjusted under 35 U.S.C. 154(b) by 0 days.

(21) Appl. No.: 16/133,271

(22) Filed: Sep. 17, 2018

(65) Prior Publication Data

US 2019/0083427 A1    Mar. 21, 2019

Related U.S. Application Data

(63) Continuation of application No. 15/503,642, filed as application No. PCT/IB2015/056090 on Aug. 11, 2015, now Pat. No. 10,117,842.

(60) Provisional application No. 62/036,488, filed on Aug. 12, 2014.

(51) Int. Cl.
| | | |
|---|---|---|
| A61K 31/19 | (2006.01) | |
| A61K 47/02 | (2006.01) | |
| A61K 9/00 | (2006.01) | |
| A61K 9/08 | (2006.01) | |
| A61P 9/10 | (2006.01) | |
| A61B 17/12 | (2006.01) | |
| A61B 17/122 | (2006.01) | |

(52) U.S. Cl.
CPC ............ *A61K 31/19* (2013.01); *A61K 9/0019* (2013.01); *A61K 9/08* (2013.01); *A61K 47/02* (2013.01); *A61P 9/10* (2018.01); *A61B 17/122* (2013.01); *A61B 17/12109* (2013.01)

(58) Field of Classification Search
CPC ............ A61B 17/12109; A61B 17/122; A61K 31/19; A61K 47/02; A61K 9/0019; A61K 9/08
See application file for complete search history.

(56) References Cited

U.S. PATENT DOCUMENTS

| 6,972,175 B2 | 12/2005 | Pinsky et al. |
| 2008/0175935 A1 | 7/2008 | Kern |
| 2010/0216883 A1 | 8/2010 | Bassaganya-Riera et al. |
| 2011/0054033 A1 | 3/2011 | Bassaganya-Riera et al. |

FOREIGN PATENT DOCUMENTS

| KR | 2003/0057205 | 7/2003 |
| WO | WO 2016/024211 | 2/2016 |

OTHER PUBLICATIONS

"Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Jul. 2005, 30 pages J:\!GUIDANC\5541fnlclnl.doc.

(Continued)

*Primary Examiner* — Savitha M Rao
(74) *Attorney, Agent, or Firm* — Fish & Richardson P.C.

(57) ABSTRACT

This document provides methods and materials for reducing ischemia-reperfusion injury. For example, methods and materials for administering ABA to reduce tissue injury caused by reperfusion following ischemia are provided.

10 Claims, 7 Drawing Sheets

(56) References Cited

OTHER PUBLICATIONS

Abdelrahman et al., "Beneficial effects of PPAR-gamma ligands in ischemia-reperfusion injury, inflammation and shock," Cardiovascular Research, Mar. 2005, 65:772-781.
Bassaganya-Riera et al., "Mechanisms of Action and Medicinal Applications of Abscisic Acid," Current Medicinal Chemistry, 2010, 12 pages.
Bodrato et al., "Abscisic Acid Activates the Murine Microglial Cell Line N9 through the Second Messenger Cyclic ADP-ribose," The Journal of Biological Chemistry, ASBMB, dated May 29, 2009, pp. 14777-14787.
Bruzzone et al., "Abscisic acid is an endogenous cytokine in human granulocytes with cyclic ADP-ribose as second messenger," PNAS, dated Apr. 3, 2007, 5759-5764.
Bruzzone et al., "Abscisic acid ameliorates the systemic sclerosis fibroblast phenotype in vitro," Biochemical and Biophysical Research Communications, 2012, 70-74.
Bruzzone et al., "Abscisic Acid Is an Endogenous Stimulator of Insulin Release from Human Pancreatic Islets with Cyclic ADP Ribose as Second Messenger," The Journal of Biological Chemistry, dated Nov. 21, 2008, pp. 32188-32197.
Bruzzone et al., "The plant hormone abscisic acid increases in human plasma after hyperglycemia and stimulates glucose consumption by adipocytes and myoblasts," The FASEB Journal, Mar. 2012, 1251-1260.
Grozio et al., "Functional characterization of a synthetic abscisic acid analog with anti-inflammatory activity on human granulocytes and monocytes," Biochemical and Biophysical Research Communications, 2011, 696-701.
Guri et al., "Abscisic acid ameliorates atherosclerosis by suppressing macrophage and CD4+ T cell recruitment into the aortic wall," Journal of Nutritional Biochemistry, 2010, 1178-1185.
Guri et al., "Dietary abscisic acid ameliorates glucose tolerance and obesity-related inflammation in db/db mice fed high-fat diets," Clinical Nutrition, 2007, 107-116.
International Preliminary Report on Patentability in International Application No. PCT/IB2015/056090, dated Feb. 23, 2017, 6 pages.
International Search report and written Opinion for international Application No. PCT/IB2015/056090, dated Oct. 19, 2015, 9 pages.
International Search Report and Written Opinion in International Application No. PCT/IB2016/054699, dated Nov. 7, 2016, 12 pages.
Le Page-Degivery et al., Presence of abscisic acid, a phytohormone, in the mammalian brain, PNAS, Feb. 1986, pp. 1155-1158.
Magnone et al., "Abscisic Acid Released by Human Monocytes Activates Monocytes and Vascular Smooth Muscle Cell Responses Involved in Atherogenesis," The Journal of Biological Chemistry, ASBMB, dated Jun. 26, 2009, pp. 17808-17818.
Magnone et al., "Autocrine abscisic acid plays a key role in quartz-induced macrophage activation," The FASEB Journal, Mar. 2012, 1261-1271.
Misra et al., "The Role of Superoxide Anion in the Autoxidation of Epinephrine and Simple Assay for Superoxide Dismutase," The Journal of Biological Chemistry, dated May 25, 1972, pp. 3170-3175.
Ohkawa et al., "Assay for lipid peroxides in animal tissues by thiobarbituric acid reaction," Analytical Biochemistry, 1979, 95:351-358.
Saat et al., "Improving the outcome of kidney transplantation by ameliorating renal ischemia reperfusion injury: lost in translation?," Journal of Translational Medicine, 2016, 9 pages.
Salvadori et al., "Update on ischemia-reperfusion injury in kidney transplantation: Pathogenesis and treatment," World Journal of Transplantation, dated Jun. 24, 2015, pp. 52-67.
Scarfi et al. "The Plant Hormone Abscisic Acid Stimulates the Proliferation of Human Hemopoietic Progenitors Through the Second Messenger Cyclic ADP-Ribose," Stem Cells, 2009, pp. 2469-2477.
Scarfi et al., "Cyclic ADP-Ribose-Mediated Expansion and Stimulation of Human Mesenchymal Stem Cells by the Plant Hormone Abscisic Acid," Stem Cells, 2008, 2855-2864.
Sedlak et al., "Estimation of total, protein-bound, and nonprotein sulfhydryl groups in tissue with Ellman's reagent," Analytical Biochemistry, 1968, 25:192-205.
Sturla et al., "LANCL2 is Necessary for Abscisic Acid Binding and Signaling in Human Granulocytes and in Rat Insulinoma Cells," The Journal of Biological Chemistry, dated Oct. 9, 2009, pp. 28045-28057.
Tossi et al., "ABA says No to UV-B: a universal response?," Trends in Plant Science, Sep. 2012, 510-517.
Viladomiu et al., "Nutritional protective mechanisms against gut inflammation," Journal of Nutritional Biochemistry, 2013, 929-939.

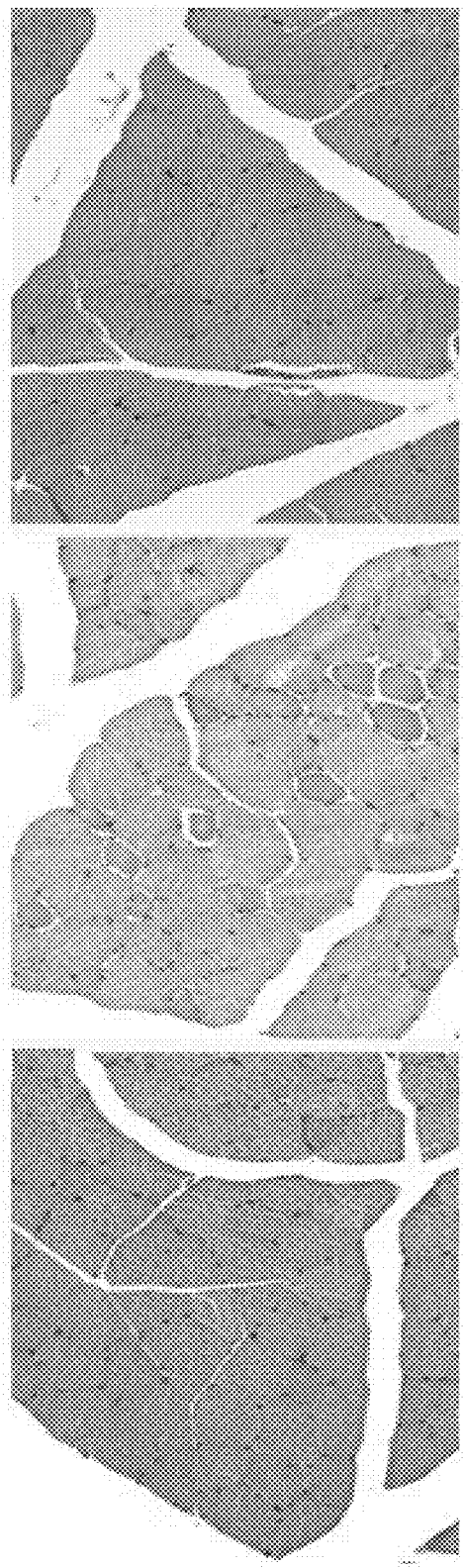

METHODS AND MATERIALS FOR REDUCING ISCHEMIA-REPERFUSION INJURY

CROSS REFERENCE TO RELATED APPLICATIONS

This application is a continuation of U.S. patent application Ser. No. 15/503,642, filed Feb. 13, 2017, which is a national stage application under 35 U.S.C. § 371 and claims the benefit of International Patent Application No. PCT/IB2015/056090, filed Aug. 10, 2015, which claims the benefit of U.S. Provisional Ser. No. 62/036,488, filed Aug. 12, 2014. The disclosure of the prior applications are considered part of (and are incorporated by reference in) the disclosure of this application.

BACKGROUND

1. Technical Field

This document relates to methods and materials for reducing ischemia-reperfusion injury. For example, this document relates to administering abscisic acid to reduce tissue injury caused by reperfusion following ischemia.

2. Background Information

Ischemia is a restriction in blood supply to tissues, which causes a shortage of elements needed for the tissues to survive such as oxygen and glucose. Surprisingly, the restoration of the physiological blood flow (e.g., reperfusion) causes further tissue lesions in many cases. See, e.g., Hausenloy and Yellon, *J. Clin. Invest.*, 123(1):92-100 (2013). An excessive inflammatory response is believed to play an essential role in the pathogenesis of this ischemia-reperfusion injury. For example, during the reperfusion of ischemic tissue, the primary tissue lesions are the consequences of an overproduction of reactive oxygen species that can result in oxidative damage such as lipid peroxidation, protein oxidation, and DNA damage. In some cases, this leads to the initiation of cell death (e.g., apoptosis or necrosis). Furthermore, reactive oxygen species can activate certain downstream signaling pathways that up-regulate the expression of genes encoding pro-inflammatory proteins.

These local and systemic inflammatory responses caused by reperfusion following ischemia can lead to clinical symptoms and pathologies like lung failure (e.g., acute respiratory distress syndrome (ARDS)), renal insufficiency, cardiac arrhythmias, and skeletal muscle revascularization oedema. These clinical complications can significantly worsen the survival chances of patients. Thus, ischemia-reperfusion injury is an existing serious condition in the aftermath of many diseases and traumatic injuries.

SUMMARY

This document provides methods and materials for reducing ischemia-reperfusion injury. For example, this document provides methods and materials for administering abscisic acid to reduce tissue injury caused by reperfusion following ischemia. Abscisic acid (ABA) is also known as (2Z,4E)-5-[(1S)-1-hydroxy-2,6,6-trimethyl-4-oxocyclohex-2-en-1-yl]-3-methylpenta-2,4-dienoic acid and (2Z,4E)-(S)-5-(1-hydroxy-2,6,6-trimethyl-4-oxo-2-cyclohexen-1-yl)-3-methyl-2,4-pentanedienoic acid.

As described herein, mammals suffering from ischemia can be administered ABA in a manner that reduces the severity of tissue or cell injury following reperfusion of the ischemic tissue. In some cases, ABA can be administered to a mammal experiencing ischemia before, during, or after reperfusion of the ischemic tissue. For example, a human patient undergoing a surgical procedure that requires stopping or reducing the flow of blood to particular tissue can be administered ABA about 10 minutes to 60 minutes prior to reperfusion to reduce the severity of ischemia-reperfusion injury. In some cases, it can be important to induce reperfusion as quickly as possible such as when treating a human patient suffering from an acute ischemic condition (e.g., brain stroke, myocardial infarct, or acute limb or mesenteric ischemia). In these cases, ABA can be administered to the patient when the ischemia is first recognized prior to reperfusion, during reperfusion, or shortly after reperfusion is established (e.g., about 1 to 120 minutes after reperfusion).

The use of ABA as described herein can help reduce damage to tissue and cellular architecture following reperfusion. For example, administering ABA to a human who experienced ischemia can help reduce the level of damage to tissue and cellular architecture such that minimal extracellular oedema (e.g., minimal fiber separation) and a near complete absence of intercellular vacuolization occurs following reperfusion as compared to that which occurs in a comparable human not administered ABA. Having the ability to reduce ischemia-reperfusion injury in mammals can allow clinicians to treat ischemia effectively and in a cost effective manner and can allow the mammals to recover quicker and with less lasting effects of the ischemia.

In general, one aspect of this document features a method for treating ischemia to reduce the level of ischemia-reperfusion injury that results within a mammal from the ischemia. The method comprises, or consists essentially of, administering a composition comprising abscisic acid to the mammal following ischemia, wherein the level of ischemia-reperfusion injury of the mammal is reduced following the administering step as compared to the level of ischemia-reperfusion injury within a mammal not administered the composition following ischemia. The mammal can be a human. The ischemia can be ischemia induced by a surgeon during a surgery. The ischemia can be ischemia caused by a medical condition. The medical condition can be atherosclerotic stenosis, anemia, thrombosis, embolism, traumatic injuries, or stroke. The composition can comprise between 5 and 95 percent by weight the abscisic acid. The composition can comprise between 20 and 80 percent by weight the abscisic acid. The composition can comprise between 0.1 and 10 percent by weight the abscisic acid. The composition can further comprise a saline solution. The administration can comprise an intravenous administration.

In another embodiment, this document features a method for performing surgery within a mammal. The method comprises, or consists essentially of, (a) applying an occlusion to a blood vessel within the mammal to create ischemic tissue within the mammal, (b) administering a composition comprising abscisic acid to the mammal, and (c) removing the occlusion to restore blood flow to the ischemic tissue. The mammal can be a human. The surgery can be an embolectomy, a thrombectomy, a bypass surgery, an angioplasty, a carotid surgery, a coronary artery surgery, or an aortic surgery. The occlusion can be applied using a surgical clamp. The blood vessel can be an artery. The ischemic tissue can be brain tissue, myocardial tissue, or skeletal muscle tissue. The composition can comprise between 5 and 95 percent by weight the abscisic acid. The composition can comprise between 20 and 80 percent by weight the abscisic acid. The composition can comprise between 0.1 and 10 percent by weight the abscisic acid. The composition can further comprise saline solution. The administration can comprise an intravenous administration. The method can comprise administering the composition to the mammal from about 10 minutes to about 60 minutes before the occlusion is removed. The administering can result in a final concentration of abscisic acid within the blood of the mammal that is from about 5 µM to about 10 mM.

In another embodiment, this document features a method for treating a mammal presenting with an occlusion of a blood vessel in a manner that creates ischemic tissue within the mammal. The method comprises, or consists essentially of, (a) identifying the mammal as having the occlusion, (b) administering a composition comprising abscisic acid to the mammal, and (c) removing the occlusion to restore blood flow to the ischemic tissue. The mammal can be a human. The blood vessel can be an artery. The ischemic tissue can be brain tissue, myocardial tissue, or skeletal muscle tissue. The composition can comprise between 5 and 95 percent by weight the abscisic acid. The composition can comprise between 20 and 80 percent by weight the abscisic acid. The composition can comprise between 0.1 and 10 percent by weight the abscisic acid. The composition can further comprise saline solution. The administration can comprise an intravenous administration. The method can comprise administering the composition to the mammal from about 10 minutes to about 60 minutes before the occlusion is removed. The method can comprise administering the composition to the mammal after the occlusion is removed. The administering can result in a final concentration of abscisic acid within the blood of the mammal that is from about 5 µM to about 10 mM.

In another embodiment, this document features abscisic acid and compositions comprising abscisic acid for use as a medicament. The composition for use as a medicament can comprise between 5 and 95 percent by weight said abscisic acid, between 20 and 80 percent by weight said abscisic acid, or between 0.1 and 10 percent by weight said abscisic acid. The composition can comprise a saline solution. The abscisic acid and composition comprising abscisic acid can be for intravenous administration.

In some cases, this document features abscisic acid and compositions comprising abscisic acid for reducing ischemia-reperfusion injury. The abscisic acid and compositions comprising abscisic acid for reducing ischemia-reperfusion injury can be for reducing ischemia-reperfusion injury in a mammal (e.g., a human). The abscisic acid and compositions comprising abscisic acid for reducing ischemia-reperfusion injury can be for administration following ischemia. The ischemia can be ischemia induced by a surgeon during a surgery. The ischemia can be caused by a medical condition. The medical condition can be atherosclerotic stenosis, anemia, thrombosis, embolism, traumatic injuries, or stroke. The composition comprising abscisic acid for reducing ischemia-reperfusion injury can comprise between 5 and 95 percent by weight said abscisic acid, between 20 and 80 percent by weight said abscisic acid, or between 0.1 and 10 percent by weight said abscisic acid. The composition can comprise a saline solution. The abscisic acid and compositions comprising abscisic acid for reducing ischemia-reperfusion injury can be for intravenous administration. The abscisic acid and compositions comprising abscisic acid for reducing ischemia-reperfusion injury can be for administration about 10 minutes to 60 minutes prior to reperfusion.

In another embodiment, this document features an ex vivo or in vitro method comprising: administering abscisic acid or a composition comprising abscisic acid to ischemic cells, ischemic tissue, or an ischemic organ of a mammal. The mammal can be a human. Optionally, an occlusion can be applied to a blood vessel prior to administering the composition. Further optionally, said occlusion can be removed after administering the composition. The composition can be administered from about 10 minutes to about 60 minutes before the occlusion is removed. The step of administering, and if present the further steps of applying an occlusion and of removing said occlusion, can be performed ex vivo or in vitro.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1A is a photograph of aorta occlusion. FIG. 1B is a photograph taken during the ischemic period. FIG. 1C is a photograph taken during the injection of ABA into the mesenteric vein during ischemia. FIG. 1D is a photograph taken during the remaining time of the ischemic period. FIG. 1E is a photograph taken during release of the clamp. FIG. 1F is photograph taken during reperfusion.

FIGS. 7A-7C are photographs of skeletal muscle morphology shown in cross-sections stained with hematoxylin and eosin: FIG. 7A a sham operated control without ischemia-reperfusion treatment, FIG. 7B ischemic reperfused operated control, and FIG. 7C ABA-treated ischemic-reperfused tissue, where ABA was injected intravenously at a final concentration of 100 µM in the $20^{th}$ minute of a one-hour long ischemic period, which was followed by a one-hour reperfusion.

DETAILED DESCRIPTION

Figure 1A:
FIGS. 1A-1F are photographs of an operational method for inducing ischemia and performing reperfusion in rats.
Figure 1B:
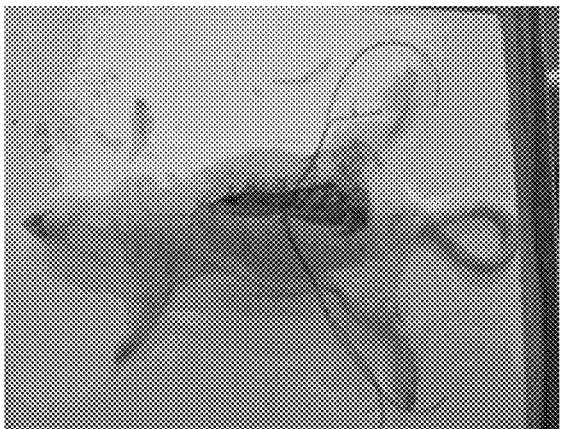
Figure 1C:
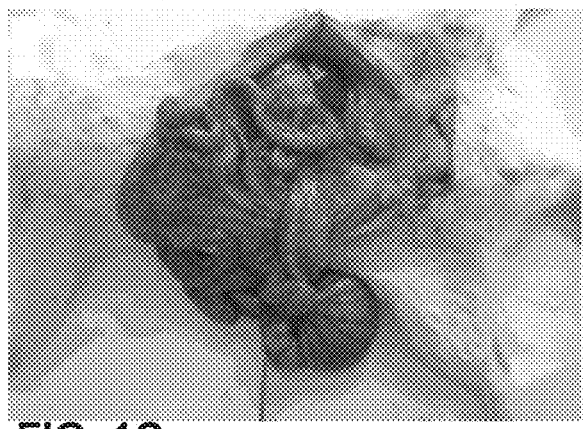
Figure 1D:
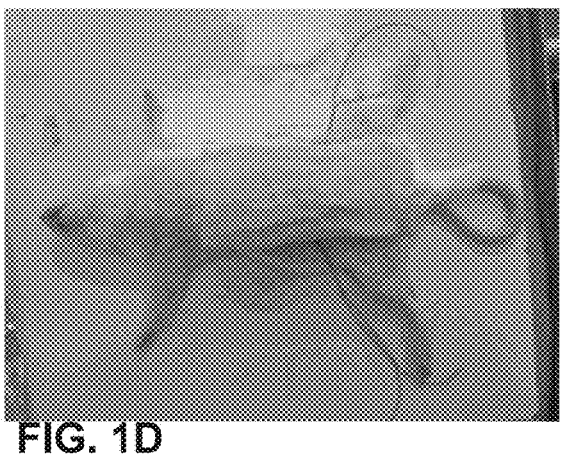
Figure 1E:
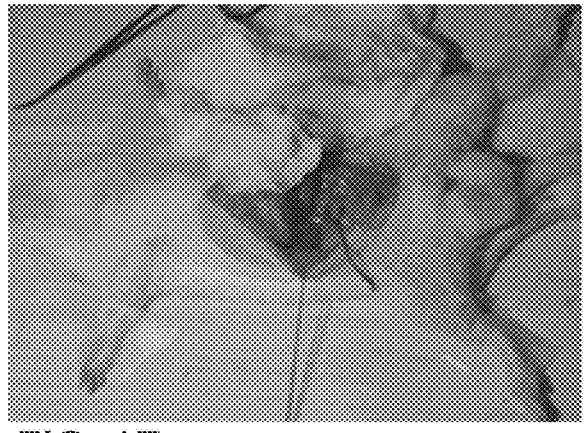
Figure 1F:
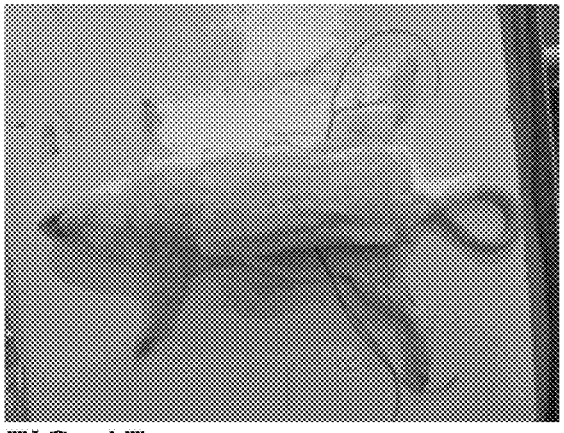

This document provides methods and materials for reducing ischemia-reperfusion injury. For example, in one embodiment, this document provides methods and materials for using ABA to reduce ischemia-reperfusion injury in a mammal undergoing a surgical procedure that requires stopping or reducing the flow of blood to particular tissue. In some cases, a mammal can be scheduled to undergo a surgery (e.g., a vascular surgery, a carotid surgery, a coronary artery surgery, or an aortic surgery) that requires stopping or reducing the flow of blood to particular tissue (e.g., brain tissue, myocardial tissue, or skeletal muscle tissue). As part of the surgical process, the surgeon can surgically occlude one or more blood vessels, which results in ischemia, and then remove the occlusion to restore blood flow. At any point during this surgical process, ABA can be administered to the mammal to reduce the ischemia-reperfusion injury that normally occurs following reperfusion. For example, after the surgical process starts but before one or more blood vessels are occluded (e.g., about 10 seconds to about 120 minutes prior to occluding one or more blood vessels), ABA can be administered to the mammal to reduce the severity of ischemia-reperfusion injury. In some cases, ABA can be administered during the surgical process from about 10 seconds to about 90 minutes (e.g., from about 10 seconds to about 60 minutes, from about 10 seconds to about 30 minutes, from about 10 seconds to about 15 minutes, from about 10 seconds to about 10 minutes, from about 10 seconds to about 5 minutes, from about 10 seconds to about 2 minutes, or from about 10 seconds to about 1 minute) prior to occluding one or more blood vessels.

In some cases, ABA or a composition that includes ABA can be administered to a mammal (e.g., a human) as described herein to reduce the level of ischemia-reperfusion injury within the mammal as compared to the level of ischemia-reperfusion injury within a mammal not administered ABA or the composition that includes ABA. For example, the level of ischemia-reperfusion injury experienced by a mammal administered ABA as described herein can be at least 5, 10, 15, 20, 25, 30, 35, 40, 45, 50, 55, 60, 65, 70, 75, 80, 85, 90, 95 or 100 percent less than that level experienced by a comparable mammal not administered ABA.

In some cases, ABA can be administered to a mammal during the surgical process while one or more blood vessels are being surgically occluded. For example, ABA can be administered to the mammal as a single administration (e.g., an injection) while one or more blood vessels are being surgically occluded. In another embodiment, the mammal can be provided an IV solution containing ABA that delivers ABA to the mammal the entire time one or more blood vessels are being surgically occluded. In some cases, ABA can be administered during the surgical process at the same time that reperfusion is initiated.

In some cases, ABA can be administered to a mammal during the surgical process but after removal of one or more surgically applied occlusions. For example, ABA can be administered during the surgical process from about 1 second to about 90 minutes (e.g., from about 1 second to about 60 minutes, from about 1 second to about 30 minutes, from about 1 second to about 15 minutes, from about 1 second to about 10 minutes, from about 1 second to about 5 minutes, from about 1 second to about 2 minutes, or from about 1 second to about 1 minute) following removal of one or more surgically applied occlusions.

In some cases, ABA can be administered during the entire surgical process. For example, a mammal can be provided an IV solution containing ABA that delivers ABA to the mammal the entire time during a surgery that includes surgically occluding one or more blood vessels.

In some cases, ABA can be administered before beginning a surgery that involves surgically occluding one or more blood vessels. For example, ABA can be administered to a mammal from about 1 minute to about 48 hours before the surgery begins (e.g., from about 5 minutes to about 48 hours, from about 15 minutes to about 48 hours, from about 30 minutes to about 48 hours, from about 1 hour to about 48 hours, from about 2 hours to about 48 hours, from about 3 hours to about 48 hours, from about 4 hours to about 48 hours, from about 6 hours to about 48 hours, from about 8 hours to about 48 hours, from about 10 hours to about 48 hours, from about 12 hours to about 48 hours, from about 24 hours to about 48 hours, from about 1 minute to about 36 hours, from about 1 minute to about 24 hours, from about 1 minute to about 12 hours, from about 1 minute to about 8 hours, from about 1 minute to about 6 hours, or from about 1 minute to about 2 hours before the surgery begins) to reduce the severity of ischemia-reperfusion injury.

In some cases, ABA can be administered before beginning a surgery and during the entire surgical process. For example, a mammal can be administered ABA (e.g., by injection) prior to starting a surgery that includes surgically occluding one or more blood vessels and then provided an IV solution containing ABA that delivers ABA to the mammal the entire time during a surgery.

In some cases, ABA can be administered after completion of a surgery that involves surgically occluding one or more blood vessels. For example, ABA can be administered to a mammal from about 1 minute to about 1 week after the surgery is completed (e.g., from about 5 minutes to about 1 week, from about 15 minutes to about 1 week, from about 30 minutes to about 1 week, from about 1 hour to about v, from about 2 hours to about 1 week, from about 3 hours to about 1 week, from about 4 hours to about 1 week, from about 6 hours to about 1 week, from about 8 hours to about 1 week, from about 10 hours to about 1 week, from about 12 hours to about 1 week, from about 24 hours to about 1 week, from about 1 minute to about 3 days, from about 1 minute to about 48 hours, from about 1 minute to about 24 hours, from about 1 minute to about 12 hours, from about 1 minute to about 8 hours, from about 1 minute to about 6 hours, from about 1 day to about 5 days, or from about 2 days to about 4 days after the surgery is completed) to reduce the severity of ischemia-reperfusion injury.

In another embodiment, this document provides methods and materials for using ABA to reduce ischemia-reperfusion injury in a mammal suffering from an ischemic condition (e.g., an acute ischemic condition). For example, a mammal diagnosed as having an ischemic condition can be treated to restore blood flow to the ischemic tissue. As part of this treatment process, a doctor can medically or surgically remove an occlusion to restore blood flow within the mammal. Examples of medical treatments for removing an occlusion to restore blood flow within the mammal include, without limitation, administering an anticoagulant (e.g., continuous IV of unfractionated heparin), thrombolysis, embolectomy, bypass surgery, or angioplasty. Examples of surgical treatments for removing an occlusion to restore blood flow within the mammal include, without limitation, surgical revascularization such as embolectomy, thrombectomy, bypass surgery, and angioplasty. At any point during the diagnosis or treatment process, ABA can be administered to the mammal to reduce the ischemia-reperfusion injury that normally occurs following reperfusion. For example, ABA can be administered to the mammal when the mammal first presents with an ischemic condition, when the mammal is diagnosed with an ischemic condition, while the mammal is being treated for the ischemic condition, or after treatment of the ischemic condition. In one embodiment, ABA can be administered to the mammal as a single administration (e.g., an injection) alone or in combination with other compounds after the treatment process started but before an occlusion is removed. In another embodiment, the mammal can be provided an IV solution containing ABA that delivers ABA to the mammal after the treatment process started but before an occlusion is removed.

In some cases, ABA can be administered to a mammal during the treatment process but after removal of one or more occlusions. For example, ABA can be administered during the treatment process from about 1 second to about 90 minutes (e.g., from about 1 second to about 60 minutes, from about 1 second to about 30 minutes, from about 1 second to about 15 minutes, from about 1 second to about 10 minutes, from about 1 second to about 5 minutes, from about 1 second to about 2 minutes, or from about 1 second to about 1 minute) following restoration of blood flow to the ischemic tissue.

In some cases, ABA can be administered during the entire treatment process. For example, a mammal can be provided an IV solution containing ABA that delivers ABA to the mammal the entire time during a treatment process that includes medically or surgically removing an occlusion present in one or more blood vessels.

In some cases, ABA can be administered before beginning a treatment process that involves medically or surgically removing one or more occlusions. For example, ABA can be administered to a mammal from about 1 minute to about 48 hours before a surgery begins (e.g., from about 5 minutes to about 48 hours, from about 15 minutes to about 48 hours, from about 30 minutes to about 48 hours, from about 1 hour to about 48 hours, from about 2 hours to about 48 hours, from about 3 hours to about 48 hours, from about 4 hours to about 48 hours, from about 6 hours to about 48 hours, from about 8 hours to about 48 hours, from about 10 hours to about 48 hours, from about 12 hours to about 48 hours, from about 24 hours to about 48 hours, from about 1 minute to about 36 hours, from about 1 minute to about 24 hours, from about 1 minute to about 12 hours, from about 1 minute to about 8 hours, from about 1 minute to about 6 hours, or from about 1 minute to about 2 hours before a surgery begins) to reduce the severity of ischemia-reperfusion injury.

In some cases, ABA can be administered before beginning a treatment process and during the entire treatment process. For example, a mammal can be administered ABA (e.g., by injection) prior to starting a treatment process that includes medically or surgically removing one or more occlusions and then provided an IV solution containing ABA that delivers ABA to the mammal the entire time during a treatment process.

In some cases, ABA can be administered after completion of a treatment process that involves removing one or more occlusions medically or surgically. For example, ABA can be administered to a mammal from about 1 minute to about 1 week after the treatment process is completed (e.g., from about 5 minutes to about 1 week, from about 15 minutes to about 1 week, from about 30 minutes to about 1 week, from about 1 hour to about v, from about 2 hours to about 1 week, from about 3 hours to about 1 week, from about 4 hours to about 1 week, from about 6 hours to about 1 week, from about 8 hours to about 1 week, from about 10 hours to about 1 week, from about 12 hours to about 1 week, from about 24 hours to about 1 week, from about 1 minute to about 3 days, from about 1 minute to about 48 hours, from about 1 minute to about 24 hours, from about 1 minute to about 12 hours, from about 1 minute to about 8 hours, from about 1 minute to about 6 hours, from about 1 day to about 5 days, or from about 2 days to about 4 days after the treatment process is completed) to reduce the severity of ischemia-reperfusion injury.

Examples of ischemic conditions that can be treated as described herein include, without limitation, atherosclerotic stenosis, thrombosis, embolism, traumatic injuries, stroke (e.g., ischemic stroke), myocardial infarct, and anemia followed by transfusion. For example, a mammal is suffering from atherosclerotic stenosis can undergo surgical revascularization to restore blood flow to ischemic tissue and can be administered ABA as described herein to reduce the severity of ischemia-reperfusion injury within the mammal. In another example, a mammal is suffering from ischemic stroke can be administered one or more thrombolytic drugs (e.g., streptokinase, urokinase, and recombinant tissue plasminogen activators such as alteplase, reteplase, and tenecteplase) to restore blood flow to ischemic tissue and can be administered ABA as described herein to reduce the severity of ischemia-reperfusion injury within the mammal. In these cases, the ABA can be administered before blood flow is restored, during the process of restoring blood flow, or after blood flow is restored.

Examples of mammals that can be treated as described herein include, without limitation, humans, monkeys, dogs, cats, cows, horses, pigs, rats, and mice. For example, a human patient in need of a surgical procedure that requires stopping or reducing the flow of blood to particular tissue can be treated as described herein to reduce the severity of ischemia-reperfusion injury.

As described herein, administering ABA to a mammal that underwent or is about to undergo reperfusion following ischemia can reduce the severity of ischemia-reperfusion injury, can slow the progression of ischemia-reperfusion injury, can reduce the level of MDA within the mammal, can increase the level of reduced GSH within the mammal, can increase the level of SOD activity or expression within the mammal, and/or can increase the level of PPAR-γ expression within the mammal.

Any appropriate amount of ABA can be administered to a mammal as described herein. In some cases, an effective amount of ABA can be administered to a mammal that underwent or is about to undergo reperfusion following ischemia to reduce the severity of ischemia-reperfusion injury, to slow the progression of ischemia-reperfusion injury, to reduce the level of MDA within the mammal, to increase the level of reduced GSH within the mammal, to increase the level of SOD activity or expression within the mammal, and/or to increase the level of PPAR-γ expression within the mammal. The term "effective" as used herein refers to any amount that induces a desired level of reduction in ischemia-reperfusion injury, a desired level of reduction in the progression rate of ischemia-reperfusion injury, a desired level of reduction in MDA levels within the mammal, a desired level of increase in the level of reduced GSH within the mammal, a desired level of increase in the level of SOD activity or expression within the mammal, or a desired level of increase in the level of PPAR-γ expression within the mammal, while not inducing significant toxicity in the mammal. Such an amount of ABA can be determined using the methods and materials provided herein. The level of toxicity, if any, can be determined by assessing a mammal's clinical signs and symptoms before and after administering a known amount of ABA. It is noted that the effective amount of ABA administered to a mammal can be adjusted according to a desired outcome as well as the mammal's response and level of toxicity. Significant toxicity can vary for each particular mammal.

In some cases, ABA can be administered to a mammal in an amount that results in an ABA concentration within the mammal's blood that ranges from about 1 µM to about 15 mM (e.g., from about 1 µM to about 10 mM, from about 1 µM to about 5 mM, from about 1 µM to about 1 mM, from about 1 µM to about 0.9 mM, from about 1 µM to about 0.8 mM, from about 1 µM to about 0.7 mM, from about 1 µM to about 0.6 mM, from about 1 µM to about 500 µM, from about 1 µM to about 400 µM, from about 1 µM to about 300 µM, from about 1 µM to about 200 µM, from about 1 µM to about 100 µM, from about 1 µM to about 50 µM, from about 1 µM to about 10 µM, from about 5 µM to about 10 mM, from about 10 µM to about 10 mM, from about 25 µM to about 10 mM, from about 50 µM to about 10 mM, from about 75 µM to about 10 mM, from about 100 µM to about 10 mM, from about 250 µM to about 10 mM, from about 500 µM to about 10 mM, from about 750 µM to about 10 mM, from about 1 mM to about 10 mM, from about 10 µM to about 1 mM, from about 20 µM to about 750 µM, from about 25 µM to about 750 µM, from about 25 µM to about 700 µM, from about 25 µM to about 600 µM, from about 25 µM to about 500 µM, from about 25 µM to about 400 µM, from about 50 µM to about 150 µM, or from about 75 µM to about 125 µM). When calculating the amount of ABA to administer to a mammal (e.g., a human), the volume of blood estimated to be present within the mammal can be used to determine the amount of ABA to administer to have a total body ABA blood concentration. For example, about 77 mL of blood per kg of body weight can be used as an estimate for the volume of blood present within a human. In some cases, 5 mL of 100 mM ABA solution can be used to reach 100 µM ABA concentration in 5 L blood. In some cases, the U.S. Food and Drug guidelines for human dosing can be used to calculate an amount of ABA to be administered to a human based on the information provided herein (Guidance for Industry: Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005; J:\!GUIDANC\5541fnlcln1.doc).

In some cases, ABA can be administered alone as a solution designed to have a particular concentration of ABA. For example, a solution of buffered saline can be formulated to have about 4 mg of ABA per mL. In that case, about 1 µL of the formulated solution can be administered per kg of body weight. In some cases, ABA can be formulated with other components. For example, ABA can be formulated together with heparin Na, microcirculation protectors, synthetic antioxidants, or combinations thereof to form a composition that can be administered to a mammal to reduce the severity of ischemia-reperfusion injury, to slow the progression of ischemia-reperfusion injury, to reduce the level of MDA within the mammal, to increase the level of reduced GSH within the mammal, to increase the level of SOD activity or expression within the mammal, and/or to increase the level of PPAR-γ expression within the mammal.

In some cases, ABA can be chemically converted from its free base form to a pharmaceutically acceptable salt by reacting the free base with an equivalent amount of an acid or a base that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. Suitable pharmaceutically acceptable base addition salts include, for example, metallic salts including alkali metal, alkaline earth metal, and transition metal salts such as, for example, calcium, magnesium, potassium, sodium, and zinc salts. Pharmaceutically acceptable base addition salts also can include organic salts made from basic amines such as, for example, N,N'-dibenzyl-ethylenediamine, chloroprocaine, choline, diethanolamine, ethylenediamine, meglumine (N-methylglucamine), and procaine. In some cases, ABA or a pharmaceutically acceptable salt thereof provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. In some cases, preservatives, flavorings, and other additives such as, for example, antimicrobials, anti-oxidants, chelating agents, inert gases, and the like can be present. It will be appreciated that ABA or a pharmaceutically acceptable salt thereof provided herein that is to be administered to a mammal can contain zero, one, or more than one commonly known pharmaceutically acceptable carriers.

ABA or a composition that includes ABA as described herein can be administered to any part of a mammal's body. For example, ABA or a composition that includes ABA can be administered intravenously, intraarterially (e.g., via selective intra-arterial applications), orally, or intramuscularly. In some cases, the amount of ABA to be administered can be adjusted to account for a particular route of administration.

The invention will be further described in the following examples, which do not limit the scope of the invention described in the claims.

EXAMPLES

Example 1—Using ABA to Reduce Ischemia-Reperfusion Injury

Animal Care

Wistar albino rats (250-280 g) were housed two per cage in an air-filtered and light controlled (12:12 hour, light-dark cycle) room at 21±2° C. Purina™ rat chow pellets and water were provided ad libitum.

Time Course Experiment

The rats were divided randomly into four groups. The first group was a group of operated rats that underwent ischemia followed by an hour-long reperfusion without being treated with ABA (operated untreated control). The other three groups included operated rats that underwent ischemia followed by an hour-long reperfusion with an ABA treatment (intravenously; final concentration of 100 µM) either 20 minutes, 40 minutes, or 60 minutes before reperfusion. Upon completion of the one-hour reperfusion, the rats were anesthetized with intraperitoneal injection of ketamine (40 mg/kg) and diazepam (5 mg/kg) and evaluated.

Dosage Experiments

Rats were randomly divided into five groups. The first group was a group of operated rats that underwent ischemia followed by an hour-long reperfusion without being treated with ABA (operated untreated control). The other four groups included operated rats that underwent ischemia followed by an hour-long reperfusion with an intravenous ABA treatment 20 minutes before reperfusion at a final concentration of either 10 µM, 50 µM, 100 µM, or 500 µM of ABA. Upon completion of the one-hour reperfusion, the rats were anesthetized with intraperitoneal injection of ketamine (40 mg/kg) and diazepam (5 mg/kg) and evaluated.

In another dosage experiment, rats were randomly divided into five groups. The first group was a group of operated rats that underwent ischemia followed by an hour-long reperfusion without being treated with ABA (operated untreated control). The other four groups included operated rats that underwent ischemia followed by an hour-long reperfusion with an intravenous ABA treatment 40 minutes before reperfusion at a final concentration of either 10 µM, 50 µM, 100 µM, or 500 µM of ABA. Upon completion of the one-hour reperfusion, the rats were anesthetized with intraperitoneal injection of ketamine (40 mg/kg) and diazepam (5 mg/kg) and evaluated.

Occlusion of Infrarenal Aorta

Following the anesthesia, an abdominal opening technique was performed by a midline laparotomy incision. See, FIGS. 1A-F. After repositioning the intestines, the aorta came into sight and was carefully isolated. After the isolation process, the aorta was occluded for one hour (ischemic period). The clamp was released at the end of the ischemic period to start the reperfusion for one hour. Right after the one-hour reperfusion treatment period, peripheral blood samples were collected and evaluated.

Abscisic Acid (ABA) Administration

An abscisic acid solution was injected in an appropriate concentration (e.g., 10, 50, 100, or 500 µM at a final concentration) into the superior mesenteric vein at different time points (e.g., 20, 40, or 60 minutes before reperfusion of the ischemic period).

Measurement of Stress Markers

Malondialdehyde (MDA) levels were determined in anti-coagulated whole blood using a colorimetric assay as described elsewhere (Ohakawa et al., *Anal. Biochem.*, 95:351-8 (1979)). Reduced glutathione (GSH) levels, as opposed to oxidized GSH, were measured in anti-coagulated whole blood using a colorimetric assay as described elsewhere (Sedlak and Lindsay, *Anal. Biochem.*, 25:192-205 (1968)). Superoxide dismutase (SOD) enzyme activity was measured in washed red blood cells using a colorimetric assay as described elsewhere (Misra and Fridovich, *J. Biol. Chem.*, 247:3170-3175 (1972)). The levels of total thiol groups (SH; protein-bound and free sulfhydryl groups) were measured in anti-coagulated whole blood using a colorimetric assay as described elsewhere (Sedlak and Lindsay, *Anal. Biochem.*, 25:192-205 (1968)).

RNA Extraction

Total RNA was extracted from the renal tissue samples with TRI reagent (Sigma-Aldrich) according to the manufacturer's instructions.

cDNA Synthesis

Complementary DNA was synthesized from 5 µg DNaseI treated total RNA in 20 µL final volume using oligo(dT) primer and the M-MuLV reverse transcriptase from Fermentas RevertAid™ Reverse Transcriptase Kit according to the manufacturer's recommendations. The RTase was then inactivated at 70° C. for 10 minutes.

Semi-Quantitative Reverse Transcription PCR Analysis

Two microliters of synthesized and 10-times diluted cDNA samples were used for PCR amplification by 1 units of Taq DNA polymerase (Fermentas, DreamTaq™ Green DNA Polymerase) in a total volume of 20 µL under the following conditions: 95° C. for 5 min, followed by 30 cycles consisting of 30 seconds at 94° C. then 30 seconds at 60° C. (annealing temperature of PPARγ and SOD GAPDH primer pairs), 1 minute at 72° C. The procedure was ended at 72° C. for 5 minutes. The number and temperature of cycles were optimized for each specific primer pair (Integrated DNA Technologies Inc.). Fifteen microliters of the PCR products were loaded and separated on 1.2% agarose gel containing ethidium bromide for visualization and photography experiments.

Histological Analysis

Wistar albino rats (250-280 g) were sham operated (control without ischemia-reperfusion treatment), subjected to ischemia followed by reperfusion (ischemia-reperfusion control), or subjected to ischemia followed by reperfusion with ABA being injected intravenously at a final concentration of 100 µM at the 20th minute of the one hour long ischemic period, which was followed by a one-hour reperfusion. After the one-hour reperfusion periods, tissue samples were obtained from the hind limb (m. tensor fasciae latae) of the rats and fixed in 10% buffered formaldehyde prior to being processed in a paraffin-embedded block. Four-micrometer-thick sections were cut and stained with hematoxylin and eosin.

Results

Figure 2:
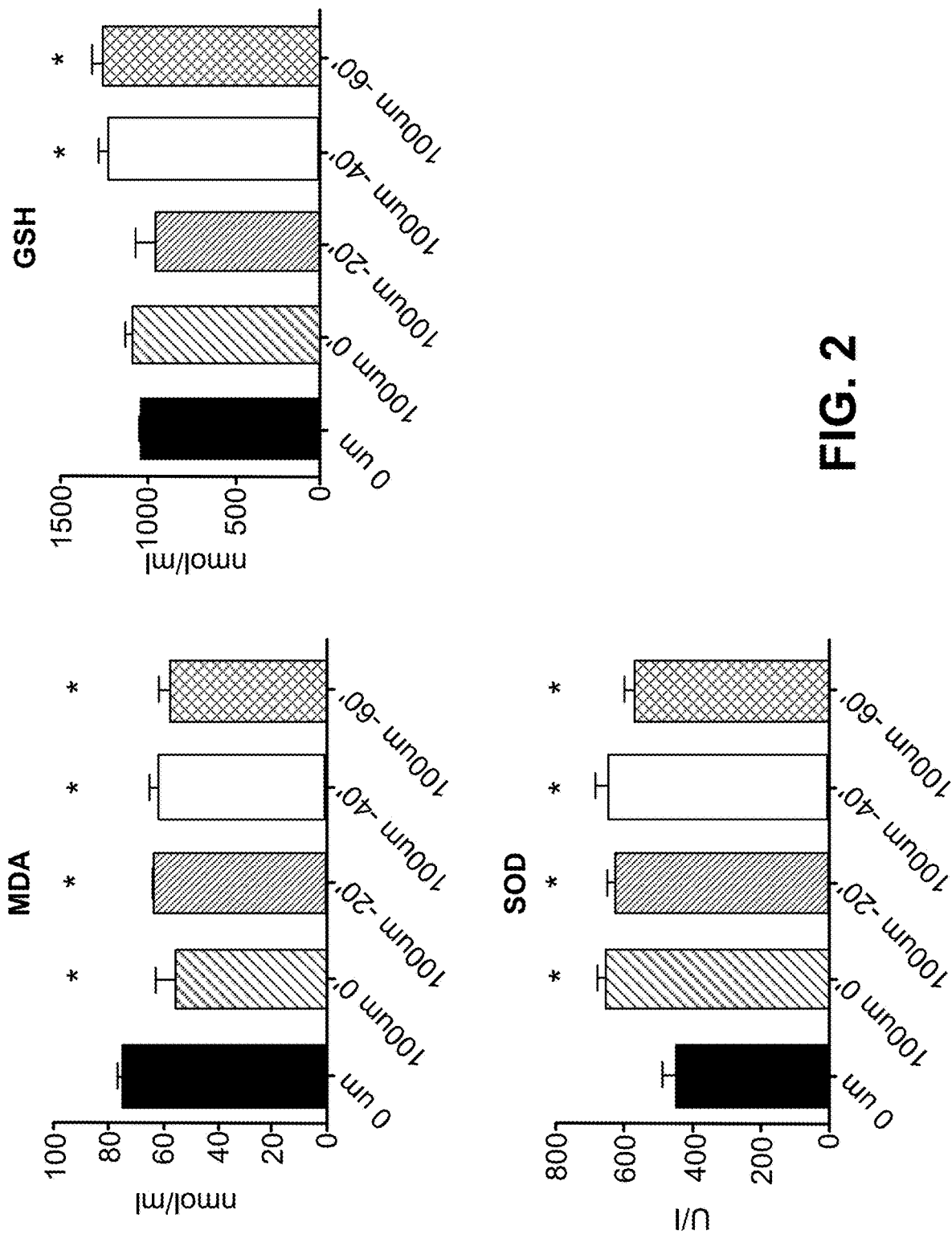
FIG. 2 contains graphs plotting the levels of malondialdehyde (MDA; nmol/mL), the levels of reduced glutathione (GSH; nmol/mL), and the levels of superoxide dismutase (SOD; U/mL) measured in blood obtained from rats one hour after initiation of reperfusion, which was initiated after a one-hour ischemia period. The rats were treated with (100 µM) or without (0 µM) ABA 0, 20, 40, or 60 minutes before initiation of the reperfusion as indicated. * represents statistical significance ($p<0.05$) as compared to control according to a one-way ANOVA analysis.

ABA was injected into the superior mesenteric vein at a final concentration of 100 µM at different time points (0, 20, 40, and 60 minutes) before reperfusion. The ABA treatment efficiently diminished the level of MDA at all time-points tested (FIG. 2). Since MDA levels are a reliable oxidative stress marker, the decline of MDA levels indicates that ABA is a potent inhibitor of oxidative stress responses during the ischemia-reperfusion process. This ability of ABA to inhibit oxidative stress responses during the ischemia-reperfusion process was further supported by the observed increases in reduced GSH levels when ABA was administered 40 or 60 minutes prior to reperfusion and the observed increases in SOD activity at all time-points tested (FIG. 2). Taken together, these results demonstrate that ABA, a compound reported to be a pro-inflammatory agent that stimulates production of, inter alia, reactive oxygen species (see, e.g., Bruzzone et al., *Proc. Natl. Acad. Sci. USA*, 104:5759-5764 (2007); Bodrato et al., *J. Biol. Chem.*, 284:14777-14787 (2009); and Bruzzone et al., *FASEB J.*, 26:1251-1260 (2012)), unexpectedly inhibits oxidative stress during the ischemia-reperfusion process and can be used to reduce the injury caused by reperfusion following ischemia. These results also demonstrate that ABA is effective when administered at the time of reperfusion or when administered before reperfusion (e.g., 20, 40, or 60 minutes before reperfusion).

Figure 3:
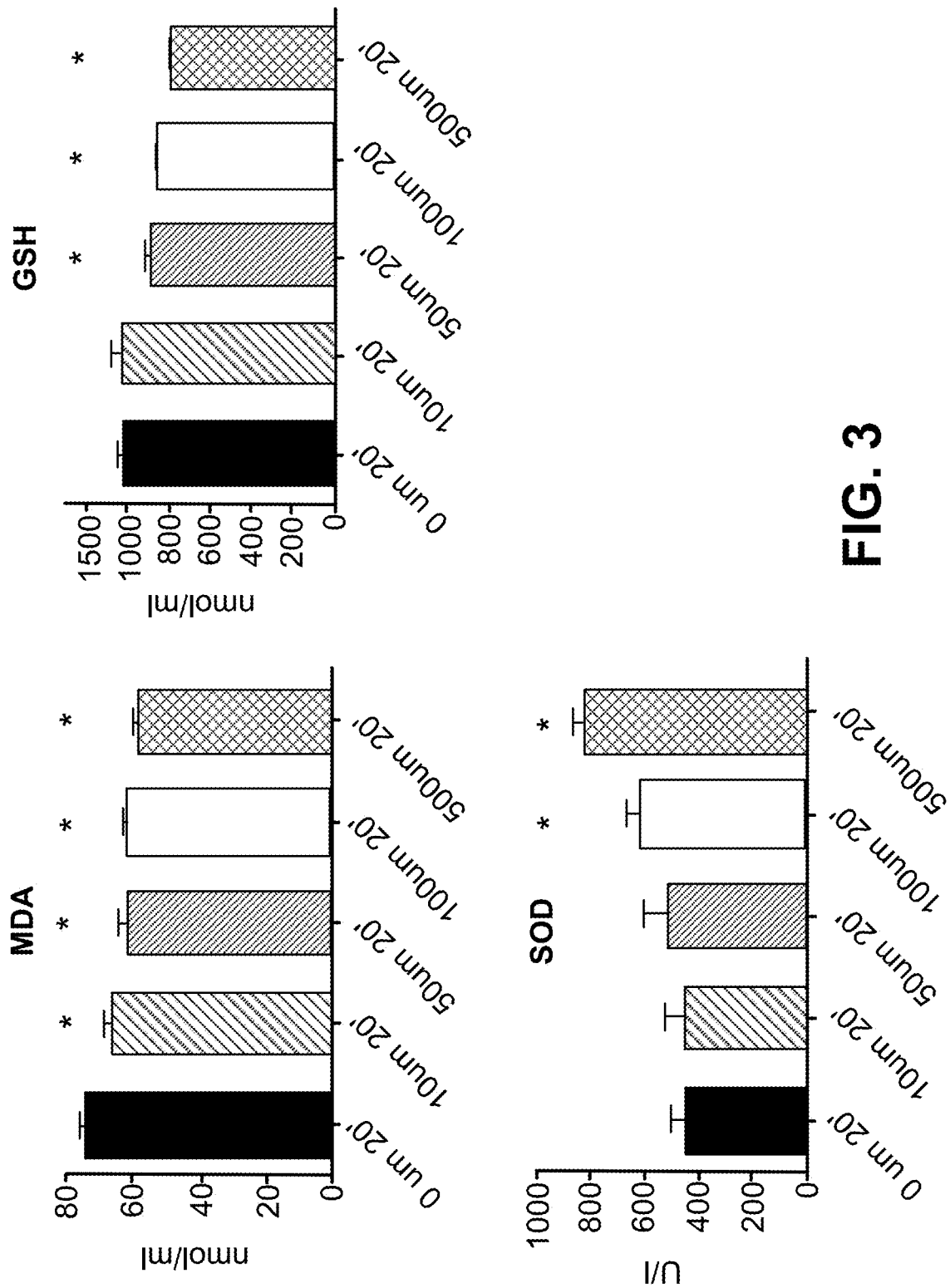
FIG. 3 contains graphs plotting the levels of MDA (nmol/mL), the levels of reduced GSH (nmol/mL), and the levels of SOD (U/mL) measured in blood obtained from rats one hour after initiation of reperfusion, which was initiated after a one-hour ischemia period. The rats were treated with 0, 10, 50, 100, or 500 µM of ABA 20 minutes before initiation of the reperfusion as indicated. * represents statistical significance ($p<0.05$) as compared to control according to a one-way ANOVA analysis.

In another experiment, ABA was injected into the superior mesenteric vein at different concentrations (0, 10, 50, 100, and 500 µM) 20 minutes before reperfusion. The ABA treatment efficiently diminished the level of MDA when injected to deliver a final concentration within the rats of 10, 50, 100, and 500 µM (FIG. 3). These results demonstrate that ABA is a potent inhibitor of oxidative stress responses during the ischemia-reperfusion process at concentrations as low as 10 µM. In addition, administration of ABA at 100 and 500 µM resulted in an increase in SOD activity (FIG. 3). Taken together, these results demonstrate that ABA is an effective inhibitor of oxidative stress during the ischemia-reperfusion process at levels as low as 10 µM. Consistent with the results from FIG. 2, administration of ABA at 50, 100, and 500 µM 20 minutes before reperfusion resulted in a decrease in the levels of reduced GSH levels. These results demonstrate that ABA may be used more effectively as an inhibitor of oxidative stress during the ischemia-reperfusion process when administered more than 20 minutes (e.g., about 30 to 60 minutes such as about 40 minutes) prior to reperfusion.

Figure 4:
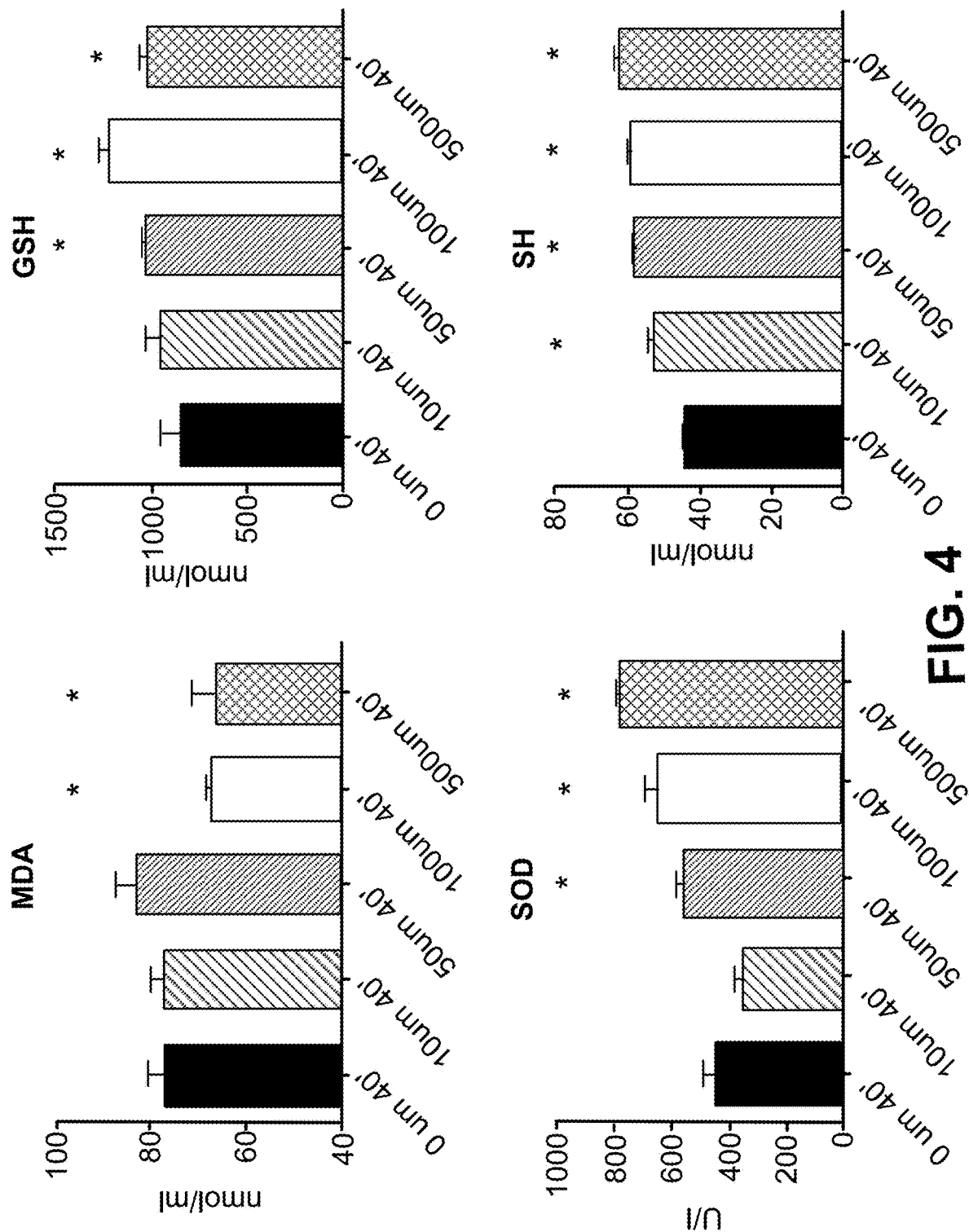
FIG. 4 contains graphs plotting the levels of MDA (nmol/mL), the levels of reduced GSH (nmol/mL), the levels of SOD (U/mL), and the levels of total thiol groups (i.e., protein-bound and nonprotein sulfhydryl groups; SH, nmol/mL) measured in blood obtained from rats one hour after initiation of reperfusion, which was initiated after a one-hour ischemia period. The rats were treated with 0, 10, 50, 100, or 500 µM of ABA 40 minutes before initiation of the reperfusion as indicated. * represents statistical significance (p<0.05) as compared to control according to a one-way ANOVA analysis.
Figure 5:
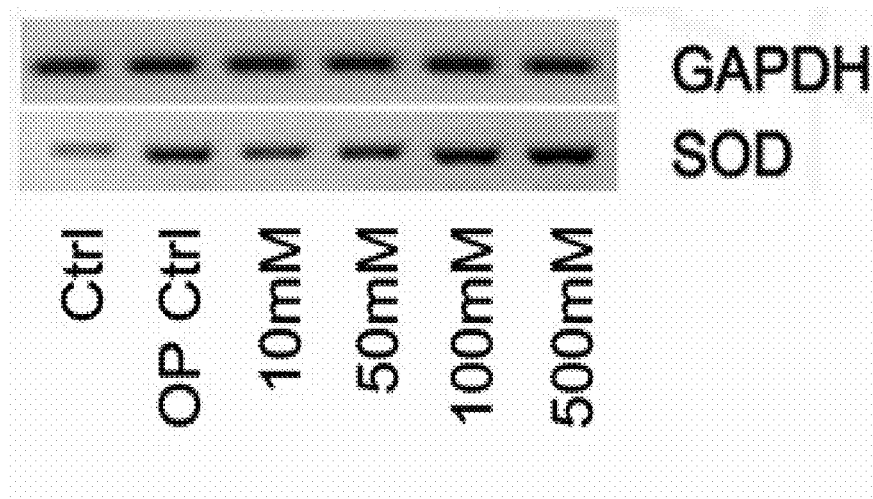
FIG. 5 is a photograph of an mRNA analysis showing the levels of SOD mRNA expression by renal tissue obtained from rats one hour after initiation of reperfusion, which was initiated after a one-hour ischemia period. The rats were treated with 0 (operation control; OP Ctrl), 10, 50, 100, or 500 µM of ABA 40 minutes before reperfusion treatment. Rats that did not undergo any operation also were used as a control (ctrl). GAPDH mRNA levels were included as another control.
Figure 6:
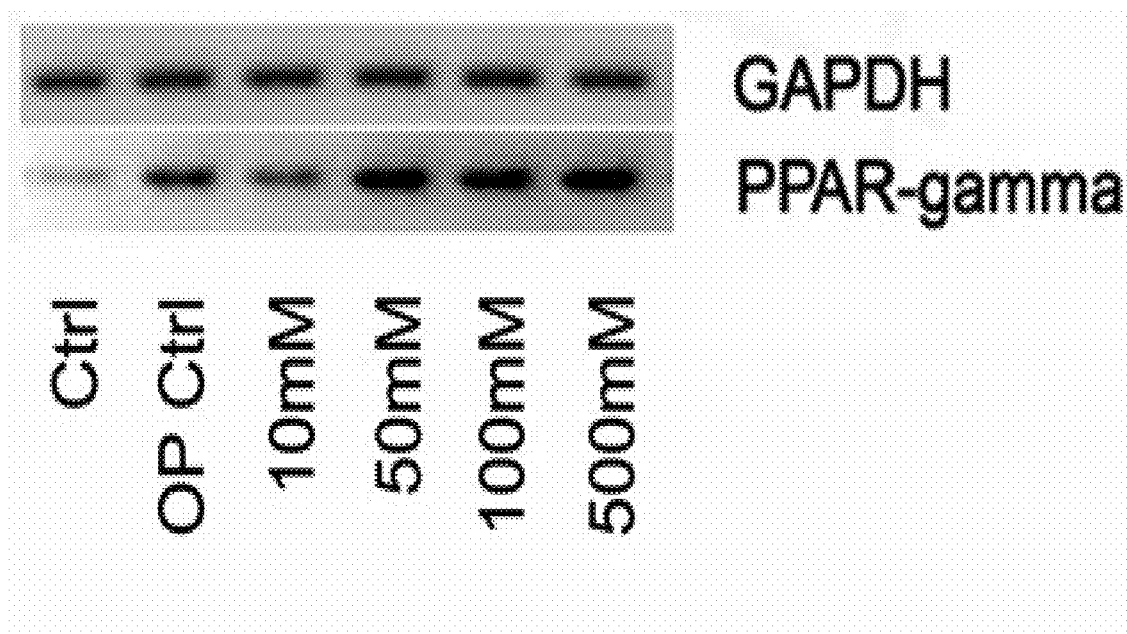
FIG. 6 is a photograph of an mRNA analysis showing the levels of PPAR-γ mRNA expression by renal tissue obtained from rats one hour after initiation of reperfusion, which was initiated after a one-hour ischemia period. The rats were treated with 0 (operation control; OP Ctrl), 10, 50, 100, or 500 µM of ABA 40 minutes before initiation of the reperfusion as indicated. Rats that did not undergo any operation also were used as a control (ctrl). GAPDH mRNA levels were included as another control.

In another experiment, ABA was injected into the superior mesenteric vein at different concentrations (0, 10, 50, 100, and 500 µM) 40 minutes before reperfusion. The ABA treatment efficiently diminished the level of MDA when injected to deliver a final concentration within the rats of 100 and 500 µM (FIG. 4). In addition, administration of ABA at 50, 100, and 500 µM resulted in an increase in the levels of reduced GSH levels. Administration of ABA at 10, 100, and 500 µM also resulted in an increase in SOD activity (FIG. 4). Further, the gene expression pattern of SOD correlated with the SOD activity results as samples for gene expression analysis taken from renal tissue exhibited increased levels of SOD mRNA expression as the amount of ABA injected 40 minutes before reperfusion increased (FIG. 5). Administration of ABA at 10, 50, 100, and 500 µM resulted in an increase in the levels of SH (FIG. 4). Thiols can help aerobic cells maintain their reducing state in an oxidizing environment. Thus, higher total thiol levels can indicate a greater reducing state of the cell. Administration of ABA 40 minutes before reperfusion also resulted in increased expression of PPAR-γ mRNA (FIG. 6). Taken together, these results confirm that ABA is an effective inhibitor of oxidative stress during the ischemia-reperfusion process at levels as low as 10 to 50 µM.

A histological assessment was performed to confirm that administration of ABA reduces ischemia-reperfusion injury in vivo. Revascularization of ischemic skeletal muscle during the reperfusion treatment can result in local and systematic complications like limb oedema, skeletal muscle necrosis, pulmonary oedema, and compartment syndrome. Skeletal muscle was used herein as a model to study the impacts of ischemia reperfusion injury in an histological assessment since its high metabolic activity makes it extremely susceptible to reperfusion injury even after a brief period of ischemia. In the sham operated control rats (without ischemia-reperfusion treatment), the physiological fiber architecture was intact (FIG. 7A). Muscular fibers were polygonal shape, contained peripherally placed nuclei, and exhibited a tightly packed structure (FIG. 7A). In ischemic reperfused operated controls, however, many of the numerous fibers lost their internal structure (e.g., round shape, small diameter). About 20 percent of the examined fibers were affected. In addition, there were signs of cellular vacuolizations, and extracellular oedema formation (FIG. 7B). ABA treatment noticeable helped to preserve of the normal tissue and cell architecture with minimal extracellular oedema (e.g., minimal fiber separation) and a near complete absence of intercellular vacuolization as compared to the ischemic reperfused operated controls (FIG. 7C).

These results demonstrate that ABA can be administered to a mammal to reduce the severity of ischemia-reperfusion injury.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating ischemia to reduce the level of ischemia-reperfusion injury that results within a mammal from said ischemia, wherein said method comprises administering a composition comprising abscisic acid to said mammal following ischemia, wherein the level of ischemia-reperfusion injury of said mammal is reduced following said administering step as compared to the level of ischemia-reperfusion injury within a mammal not administered said composition following ischemia.

2. The method of claim 1, wherein said mammal is a human.

3. The method of claim 1, wherein said ischemia is ischemia induced by a surgeon during a surgery.

4. The method of claim 1, wherein said ischemia is ischemia caused by a medical condition.

5. The method of claim 4, wherein said medical condition is atherosclerotic stenosis, anemia, thrombosis, embolism, traumatic injuries, or stroke.

6. The method of claim 1, wherein said composition comprises between 5 and 95 percent by weight said abscisic acid.

7. The method of claim 1, wherein said composition comprises between 20 and 80 percent by weight said abscisic acid.

8. The method of claim 1, wherein said composition comprises between 0.1 and 10 percent by weight said abscisic acid.

9. The method of claim 1, wherein said composition further comprises a saline solution.

10. The method of claim 1, wherein said administration comprises an intravenous administration.

\* \* \* \* \*

UNITED STATES PATENT AND TRADEMARK OFFICE
CERTIFICATE OF CORRECTION

| | | |
|---|---|---|
| PATENT NO. | : 10,610,501 B2 | Page 1 of 1 |
| APPLICATION NO. | : 16/133271 | |
| DATED | : April 7, 2020 | |
| INVENTOR(S) | : Agnes Nagy | |

It is certified that error appears in the above-identified patent and that said Letters Patent is hereby corrected as shown below:

In the Specification

Column 1, Line 12 (Approx.), Delete "10," and insert -- 11, --, therefor.

Signed and Sealed this
Sixth Day of October, 2020

Andrei Iancu
*Director of the United States Patent and Trademark Office*